United States Patent [19]

Henrie, II

[11] Patent Number: 4,818,271
[45] Date of Patent: Apr. 4, 1989

[54] PYRIDINYLUREA COMPOUNDS AND AGRICULTURAL USES

[75] Inventor: Robert N. Henrie, II, East Windsor, N.J.

[73] Assignee: FMC Corporation, Philadelphia, Pa.

[21] Appl. No.: 793,371

[22] Filed: Oct. 31, 1985

[51] Int. Cl.$^4$ .................... A01N 43/40; C07D 213/44
[52] U.S. Cl. ............................. 71/88; 71/94; 540/597; 546/193; 546/194; 546/256; 546/257; 546/258; 546/281; 546/292; 546/306
[58] Field of Search ............... 546/292, 306, 258, 256, 546/257, 281, 193, 194; 71/94, 88; 540/597

[56] References Cited

U.S. PATENT DOCUMENTS

| | | | |
|---|---|---|---|
| 3,293,257 | 12/1966 | Woods et al. | 546/306 |
| 3,330,641 | 7/1967 | Woods et al. | 71/94 |
| 3,469,965 | 4/1969 | Bruce et al. | 71/68 |
| 4,063,928 | 12/1977 | Johnston | 71/94 |
| 4,149,872 | 4/1979 | Pilgram | 546/306 |
| 4,193,788 | 3/1980 | Okamoto et al. | 71/94 |
| 4,274,639 | 7/1981 | Okamoto et al. | 71/94 |
| 4,308,054 | 12/1981 | Isogai et al. | 71/94 |
| 4,514,571 | 4/1985 | Nakai et al. | 546/306 |

OTHER PUBLICATIONS

Okomoto et al., Chem. Pharm. Bull., 29 (12), 3748-3753 (1981).
Vassilev et al., Conptes Rendus de l'Academic Balgare des Sciences, Tome 17, No. 9, 829-833 (1964); Tome 22, No. 5, 564-570 (1969)–IIa, IIb.
Vassilev et al., Comptes Rendus de l'Academic des Sciences Agricules en Bulgarie, vol. 4, No. 1, 45-54 (1971).
Vassilev et al., Fiziologiva na Rasteniyata X (2); 40-49 (1984).
Y. Isogai, Metab. Mol. Act. Cytokinius, Proc. Int. Colog. 115-28, 2-6 (9/80).
Vassilev et al., Comptes Readus de l'Academic Bulgare des Sciencies, Tome 37, Nos. 4 and 6 (1984)-517-570, 811-815.

Primary Examiner—John M. Ford
Assistant Examiner—Zinna Northington
Attorney, Agent, or Firm—Patrick C. Baker; H. Robin Ertelt

[57] ABSTRACT

Pyridinylurea compounds of the formula

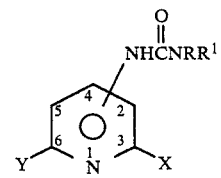

and acid addition salts thereof; wherein R is cyclo alkyl, alkenyl, or an alkyl group optionally substituted with halogen, hydroxy, cycloalkyl, alkoxy, dialkylamino or phenyl; $R^1$ is hydrogen or alkyl; R and $R^1$ together with the nitrogen atom of the $NRR^1$ group optionally define a heterocycle containing 4 to 6 ring carbon atoms; X is hydrogen, halogen, haloalkyl, alkoxy, alkylthio or alkylsulfonyl; Y is hydrogen, halogen, haloalkyl, alkoxy, alkylthio or alkylsulfonyl; and wherein the $NHCONRR^1$ group is bonded to the pyridinyl ring in the 3- or 4-position; provided that at least one of X and Y is other than hydrogen and when both R and $R^1$ are alkyl, R is 1,1-dimethylethyl or cyclopentyl and $R^1$ is methyl. The compounds are useful in agriculture as plant growth regulators.

22 Claims, No Drawings

PYRIDINYLUREA COMPOUNDS AND AGRICULTURAL USES

TECHNICAL FIELD

This invention concerns certain pyridinylurea compounds and their use in agriculture.

Representative of reseach efforts in the field are the compounds disclosed in U.S. Pat. Nos. 4,063,928 (substituted pyridinyloxy(thio)phenyl acetamides, ureas and urea derivatives), 4,193,788 (N-(2-chloro-4-pyridyl-)ureas, 4,279,639 (N-(2-sustituted-4-pyridylureas), 4,308,054 (other pyridyl ureas), 3,293,257 and 3,330,641 (1,1-dialkyl-3-pyridylureas), and 3,469,965 (urea derivatives). Synthesis and biological activity of many of the foregoing and other compounds are discussed in papers of T. Okamoto et al, Chem. Pharm. Bull., 29(12), 3748–3753 (1981); G. N. Vassilev et al, Comptes Rendus de L'Academie Bulgare des Sciences, Tome 17, No. 9, 829–833 (1964); Tome 22, No. 5, 563–567 (1969); and Tome 37, No. 6, 811–815 (1984); Vassilev et al, Comptes Rendus de l'Academic des Sciences Agricoles en Bulgarie, Vol. 4, No. 1, 45–54 (1971); and G. N. Vassilev et al, Fiziologiya na Rasteniyata X(2): 40–49 (1984).

SUMMARY OF THE INVENTION

The compounds of the invention are pyridinylureas of the formula (I):

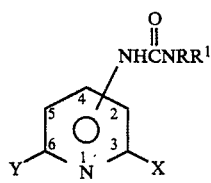

and acid addition salts thereof; wherein R is cycloalkyl, alkenyl, or alkyl optionally substituted with halogen, hydroxyl, cycloalkyl, alkoxy, dialkylamino or phenyl; $R^1$ is hydrogen or alkyl; R and $R^1$ together with the nitrogen atom of the $NRR^1$ group optionally define a non-aromatic heterocycle containing 4 to 6 ring carbon atoms; X is hydrogen, halogen, haloalkyl, alkoxy, alkylthio or alkylsulfonyl; Y is hydrogen, halogen, haloalkyl, alkoxy, alkylthio or alkylsulfonyl; and wherein the $NHCONRR^1$ group is bonded to the pyridinyl ring in the 3- or 4-position; provided that at least one of X and Y is other than hydrogen and when $R^1$ is other than hydrogen, then one of $R^1$ and, R is 1,1-dimethylethyl of cyclopentyl and —and the other of R and $R^1$ is methyl.

The compounds have utility in agriculture including plant regulatory activity in terms of one or more of stunting, dessication, axillary growth stimulation, nastic response, growth stimulation, defoliation, intumescence, negative root geotropism, darker green basal leaves, leaf alteration and retardation of senescence.

DETAILED DESCRIPTION

In formula I and except as otherwise indicated herein, R, $R^1$, X and Y may each contain 1 to 20 carbon atoms or more. The carbon chains in R, $R^1$, X and Y may be straight or branched and preferably contain 1 to 8 carbon atoms. From the standpoint of ease of synthesis 1 to 4 carbon atoms are more preferred. The cycloalkyl group preferably contains 3 to 8 carbon atoms, such as cyclopentyl, cyclohexyl and cycloheptyl. Typical alkenyl groups contain 3 to 8 carbon atoms, such as propenyl and butenyl. "Halogen" means chloro, bromo, fluoro and iodo, preferably in that order. The haloalkyl of the R, X and Y groups may contain more than one halogen atom, either the same halogen or mixed halogens, such as di- or trifluoromethyl, di- or trichloromethyl and the like. N-heterocycles defined by $NRR^1$ are non-aromatic but nevertheless include both saturated and unsaturated rings, such as pyrrolidinyl, 3-pyrrolinyl and piperidinyl.

Preferred classes of compounds of formula I are the 4-pyridinyl ureas wherein both $R^1$ and Y are hydrogen, where $R^1$ is hydrogen and both X and Y are halogen, or where both $R^1$ and Y are hydrogen and X is halogen or haloalkyl. The more preferred compounds of formula I are those wherein R is propyl, 1-methylethyl, butyl (straight or branched), cyclopentyl or cycloheptyl, $R^1$ is hydrogen, at least one of X and Y is chloro, bromo or haloalkyl such as trifluoromethyl, and the urea group is in the 4-position on the pyridinyl ring.

The acid addition salts of the compounds of formula I include organic and inorganic salts such as the hydrochlorides, sulfates, phosphates, citrates and tartrates. Preferably, but not necessarily, the salts are water soluble or water dispersible.

The compounds of formula I wherein R is other than cycloalkyl are prepared in a generally known manner by nitrating pyridine substituted with X and/or Y groups with a mixture of fuming sulfuric and nitric acids, reducing the nitro group to amino by hydrogenation over palladium or carbon, and coupling with an isocyanate (R—NCO). For preparation of compounds of formula I wherein R is alkyl or cycloalkyl and/or $R^1$ is alkyl, the amino intermediate is reacted with phenyl chloroformate to form a phenyl N-(pyridinyl)-carbamate intermediate which is then reacted with an alkyl amine (mono or di) or a cycloalkyl amine to form the corresponding monalkyl, dialkyl or cycloalkyl product. Alternatively, an aminopyridine intermediate is prepared from the corresponding ester via the Curtius reaction. The aminopyridine is then reacted with an appropriate isocyanate (R—NCO) to form the pyridinyl urea. The reactions are conducted in appropriate organic solvents with appropriate pressure and temperature controls. The work-up and isolation procedures are conventional.

Further details of synthesis are given in the patent and technical literature cited above and in representative examples below. Table I (appended lists the compounds of the examples and provides characterizing data for the synethesis examples and other compounds of the invention.

EXAMPLE 1

Synthesis of N-(2-chloro-4-pyridinyl)N'-(1-methylethyl)urea (Compound No. 7)

Step A: 2-Chloropyridine-N oxide

A stirred solution of 1656 grams (14.6 moles) of 2-chloropyridine in 4.3 liters of glacial acetic acid was warmed to 50° C. and 1.5 liters of 30% hydrogen peroxide was added dropwise. Upon completion of addition the reaction mixture was stirred at 50° C. for 45 hours during which 30% hydrogen peroxide, 500 ml at a time, was added at 5 hours, 16 hours, and 22 hours into the stirring time. The reaction mixture was concentrated to one-half volume, diluted with 5 liters of water, and again concentrated to one-half volume. The mixture was made basic with 1000 grams of sodium carbonate, and excess hydrogen peroxide was decomposed by the addition of 400 grams of sodium bisulfite. The mixture was concentrated under reduced pressure to a residual solid. The solid was extracted with two five-liter portions of chloroform. The combined extracts were dried with magnesium sulfate and filtered. The filtrate was concentrated under reduced pressure to yield 1335 grams of 2-chloropyridine-N oxide; m.p. 66°–69° C.

Step B: 2-Chloro-4-nitropyridine-N oxide

With stirring, 1.5 liters of concentrated sulfuric acid was cooled to 0° C. and 1058 grams (6.06 moles) of 2-chloropyridine-N oxide was added portionwise during a 5 hour period. The reaction mixture temperature was maintained at 5°–10° C. and 590 ml of 90% nitric acid was added dropwise. Upon completion of addition the reaction mixture was heated to 80° C. and the source of heat was removed. The exothermic reaction caused the reaction mixture temperature to rise to 115° C. During a one hour period the reaction mixture temperature fell from 115° C. to 100° C., where it was maintained for four hours with an external heat source. The reaction mixture was cooled then poured into 12 liters of ice. The resultant solid was collected by filtration and washed three times by suspension in three one-liter portions of water. The solid was dried to yield 715 grams of 2-chloro-4-nitropyridine-N oxide. The mother liquor and washes were combined and extracted with four one-liter portions of chloroform. The combined extracts were dried with potassium carbonate and filtered. The filtrate was concentrated under under reduced pressure to a residual solid. The solid was triturated in 65 ml of 2-propanol to yield an additional 94.2 grams of 2-chloro-4-nitropyridine-N oxide.

Step C: 4-Amino-2-chloropyridine

A stirred solution of 696 grams (3.99 moles) of 2-chloro-4-nitropyridine-N oxide, 700 ml of acetic acid, 700 ml of n-butyl ether, and 5.6 liters of water was cooled to 0°–5° C. and 1400 grams (25.1 mole) of iron was added in one portion. Upon completion of addition the reaction mixture temperature rose to 90° C. during a 30 minute period despite efforts to cool the reaction mixture with an ice bath. The increase in temperature was accompanied by foaming. After the foaming subsided and the reaction mixture temperature began to fall, the ice bath was removed and the reaction mixture stirred without cooling for one hour. The reaction mixture was cooled and made basic with a solution of 1400 grams of potassium hydroxide in 1.4 liters of water. The thick slurry was filtered through diatomaceous earth, and 100 grams of solid potassium hydroxide was added to the filtrate. The filtrate was extracted with one liter of diethyl ether. The filter cake was suspended in three liters of hot ethanol and filtered. The procedure was repeated twice more using two two-liter portions of hot ethyl acetate. The extracts were combined and concentrated under reduced pressure to a solid residue. The solid was dissolved in two liters of diethyl ether and the solution diluted with 2.5 liters of petroleum ether. The resultant solid was collected by filtration and dried to yield 419.6 grams of 4-amino-2-chloropyridine; m.p. 93°–95° C.

Step D: N-(2-chloro-4-pyridinyl)-N'-(1-methylethyl)urea

A solution of 2.6 grams (0.0203 mole) of 4-amino-2-chloropyridine, 0.53 gram (0.005 mole) of 1,4-diazabicyclo[2.2.2]octane (DABCO), and 3.9 ml (0.0305 mole) of (1-methylethyl)isocyanate in 20 ml of dry dimethylformamide was stirred at ambient temperature for five days. The dimethylformamide was removed under reduced pressure. The residue was taken up in 20 ml of ethanol and this was removed under reduced pressure. The procedure was repeated a second time using an additional 20 ml of ethanol. The residual oil was dried under reduced pressure at ambient temperature for 16 hours, then under reduced pressure at 60° C. for one hour. The resultant solid was triturated in hot water. The mixture was allowed to cool to ambient temperature then placed in a refrigerator where it stood for 60 hours. The solid was collected by filtration, washed with water and dried under reduced pressure for three hours at 40°–50° C. The yield of N-(2-chloro-4-pyridinyl)-N'-(1-methylethyl)urea was 4.1 grams, m.p. 142°–146.5° C. The nmr spectrum was consistent with the proposed structure.

EXAMPLE 2

Synthesis of N-(2-chloro-4-pyridinyl)N'-cyclopentylurea (Compound No. 33)

Step A: Phenyl N-(2-chloro-4-pyridinyl)carbamate

Under a nitrogen atmosphere, a stirred solution of 15.0 grams (0.117 mole) of 4-amino-2-chloropyridine and 17 ml (0.122 mole) of triethylamine in 250 ml of diethyl ether was cooled to 6° C. and 15 ml (0.120 mole) of phenyl chloroformate in 250 ml of diethyl ether was added dropwise. During the addition of the chloroformate the cooling medium surrounding the reaction vessel was removed, which allowed the reaction mixture to warm to 28° C. Upon completion of addition the reaction mixture stirred at ambient temperature for 16 hours. Analysis of the reaction mixture by TLC indicated the presence of a small amount of the starting aminopyridine. An additional 3 ml (0.024 mole) of phenyl chloroformate, 3.4 ml (0.024 mole) of triethylamine and 100 ml of diethyl ether were added and the reaction mixture was stirred an additional 24 hours. The reaction mixture was filtered and the filter cake washed with diethyl ether. The combined filtrate and wash was concentrated under reduced pressure to give 13 grams of solid product. The filter cake was dissolved in 600 ml of methylene chloride and washed with two portions of 200 ml each of water to remove triethylamine hydrochloride. The organic layer was dried with magnesium sulfate and filtered. The filtrate was concentrated under reduced pressure to a solid residue. The solid was combined with the 13 grams of solid obtained above and the combination dissolved in 1200 ml of methylene chloride. The solution was passed through a column of silica gel. Further elution was accomplished with 5% acetone-methylene chloride. The appropriate fractions were combined and concentrated under reduced pressure to a solid residue. The solid was dried in a vacuum dessicator to yield 22.0 grams of phenyl N-(2-chloro-4-pyridinyl)carbamate. The nmr spectrum was consistent with the proposed structure.

Step B: N-(2-chloro-4-pyridinyl)-N'-cyclopentylurea

A stirred solution of 3.5 grams (0.0141 mole) of phenyl N-(2-chloro-4-pyridinyl)carbamate and 1.7 ml (0.0172 mole) of cyclopentylamine in 60 ml of acetone was heated under reflux for three hours. The reaction mixture was cooled and concentrated under reduced pressure to a residual oil. The oil was dissolved in 20 ml of methylene chloride and passed through a column of silica gel. Elution was accomplished with 5% and 10% acetone-methylene chloride. The appropriate fractions were combined and concentrated under reduced pressure to yield 2.9 grams of N-(2-chloro-4-pyridinyl)-N'-cyclopentylurea; m.p. 119°–121° C. The nmr spectrum was consistent with the proposed structure.

EXAMPLE 3

Synthesis of
N-(2-chloro-4-pyridinyl)N'-(2-chloroethyl)urea (Compound No. 3)

This compound was prepared in the manner of Example 2, Step B, using 3.5 grams (0.0141 mole) of phenyl N-(2-chloro-4-pyridinyl)carbamate, 2.0 grams (0.0172 mole) of 2-chloroethylamine hydrochloride, and 2.4 ml (0.0172 mole) of triethylamine in 60 ml of acetone. The yield of N-(2-chloro-4-pyridinyl)-N'-(2-chloroethyl)urea was 2.4 grams; m.p. 87°–91° C. The nmr spectrum was consistent with the proposed structure.

EXAMPLE 4

Synthesis of
(−)-N-(2-chloro-4-pyridinyl)N'-(1-phenylethyl)urea (Compound No. 39)

To a stirred solution of 2.6 grams (0.0202 mole) of 4-amino-2-chloropyridine in 50 ml of dry dioxane was added 1.2 ml (0.010 mole) of trichloromethyl chloroformate via a syringe. The reaction mixture was warmed to reflux where it stirred for 28 hours. TLC analysis of the reaction mixture indicated that the starting aminopyridine was consumed. The reaction mixture was cooled to ambient temperature and 2.6 ml (1 eq.) of (−)-1-phenylethylamine was added. The reaction mixture stirred at ambient temperature for one hour and 5 ml of triethylamine was added. The reaction mixture was stirred at ambient temperature for 16 hours, then was poured into ice-water where it stirred for three hours. The three phase mixture was filtered to remove a white solid. The solid was washed with water and dried at 100° C. for 30 minutes in a vacuum dessicator. NMR analysis of the solid indicated it to be a by-product, N,N'-di(2-chloro-4-pyridinyl)urea. The filtrate containing an oil and an aqueous layer was placed in a separatory funnel and the layers separated. The aqueous layer was washed with diethyl ether. The wash and the oil layer were combined, dried with magnesium sulfate and filtered. The filtrate was concentrated under reduced pressure to a residual oil. The oil was dissolved in 150 ml of methylene chloride and a small amount of solid precipitate was collected by filtration. TLC analysis of the solid indicated it to be something other than the main product. The filtrate was passed through a column of silica gel. Further elution was accomplished with diethyl ether. The appropriate fractions were combined and concentrated under reduced pressure to a residual solid. The solid was dried at 50° C. for four hours in a vacuum dessicator. The yield of (−)-N-(2-chloro-4-pyridinyl)-N'-(1-phenylethyl)urea was 1.7 grams, as a solid. The nmr spectrum was consistent with the proposed structure.

EXAMPLE 5

Synthesis of
N-(2-bromo-4-pyridinyl)N'-(1-methylethyl)urea (Compound No. 44)

Step A: 2-Bromopyridine-N oxide

Trifluoroacetic acid, 150 ml, was added slowly to 42.9 grams (0.272 mole) of cooled, stirred 2-bromopyridine. Upon completion of addition 62.5 ml (0.543 mole) of 30% hydrogen peroxide was added. The reaction mixture was heated to 40°–45° C. where it stirred for 16 hours. The reaction mixture was concentrated under reduced pressure to a residue. The residue was diluted to full volume with water, concentrated under reduced pressure to a residue, and the procedure repeated twice more. The residue was diluted with water, neutralized with solid sodium bicarbonate, and excess hydrogen peroxide was destroyed with sodium metabisulfite. The mixture was extracted with methylene chloride using a continuous extractor. The extract was dried with sodium sulfate and filtered. The filtrate was concentrated under reduced pressure to yield 30.9 grams of 2-bromopyridine-N oxide as an oil. The reaction was repeated several times.

Step B: 2-Bromo-4-nitropyridine-N oxide

This compound was prepared in the manner of Example 1, Step B, using 40.9 grams (0.235 mole) of 2-bromopyridine-N oxide, 55.4 ml of concentrated fuming nitric acid and 210 ml of concentrated sulfuric acid. The yield of 2-bromo-4-nitropyridine-N oxide was 36.7 grams.

Step C: 4-Amino-2-bromopyridine under a nitrogen atmosphere, the reactants were placed in a 500 ml hydrogenation bottle in the following order: 250 ml of ethanol, 4.0 ml of Raney nickel, 28.5 grams (0.130 mole) of 2-bromo-4-nitropyridine-N oxide, and 25 ml of glacial acetic acid. The mixture was hydrogenated using a Parr hydrogenator. Upon completion of the uptake of hydrogen the reaction mixture was purged with gaseous nitrogen for one hour then filtered through diatomaceous earth. The filter cake was washed with ethanol, then water, and the mixture was concentrated under reduced pressure to a residual oil. The oil was dissolved in diethyl ether and washed twice with 10% aqueous sodium bicarbonate. The ether layer was dried with magnesium sulfate and filtered. The filtrate was concentrated under reduced pressure to a residual oil. The oil was combined with those of previous runs of this reaction to yield a total of 25.7 grams. The oil was placed on a column of silica gel and eluted with methylene chloride, then with 10% acetone-methylene chloride. The appropriate fractions were combined and concentrated under reduced pressure to yield 13.2 grams of 4-amino-2-bromopyridine. The nmr spectrum was consistent with the proposed structure.

Step D: N-(2-bromo-4-pyridinyl)-N'-(1-methylethyl)urea

This compound was prepared in the manner of Example 1, Step D, using 2.5 grams (0.0144 mole) of 4-amino-2-bromopyridine, 0.5 gram (0.004 mole) of 1,4-diazabicyclo[2.2.2]octane (DABCO), 1.8 ml (0.0187 mole) of (1-methylethyl)isocyanate in 10 ml of dimethylformamide. The yield of N-(2-bromo-4-pyridinyl)-N'-(1-methylethyl)urea was 3.7 grams; m.p. 136°–138° C. The nmr spectrum was consistent with the proposed structure.

EXAMPLE 6

Synthesis of
N-(2-propoxy-4-pyridinyl)-N'-(1-methylethyl)urea (Compound No. 47)

Steps A–C: Propyl 2-propoxypridine-4-carboxylate

This compound was prepared in a three-step route from 4-pyridinecarboxylic acid, N-oxide using methods analogous to those described by J. K. Seydel et al, J. Med. Chem., 19, 4, 483 (1976).

Steps D-F: (1,1-Dimethylethyl) N-(2-propoxy-4-pyridinyl)carbamate

This compound was prepared from propyl 2-propoxypyridine-4-carboxylate via a Curtius reaction, analogous to that described by M. T. Garcia-Lopez et al, J. Het. Chem. 19, 122 (1982).

Step G: 4-Amino-2-propoxypyridine

A solution of 4.4 grams (0.017 mole) of (1,1-dimethylethyl) N-(2-propoxy-4-pyridinyl)carbamate in 20 ml of trifluoroacetic acid was stirred at ambient temperature for one hour. The excess trifluoroacetic acid was removed under reduced pressure. The yield of 4-amino-2-propoxypyridine was 2.6 grams as an oil.

Step H: N-(2-propoxy-4-pyridinyl)-N'-(1-methylethyl)urea

This compound was prepared in the manner of Example 1, Step D, using 2.6 grams (0.017 mole) of 4-amino-2-propoxypyridine, 0.5 gram (0.004 mole) of 1,4-diazabicyclo[2.2.2]octane (DABCO), 2.2 ml (0.023 mole) of (1-methylethyl)isocyanate in 10 ml of dimethylformamide. The yield of N-(2-propoxy-4-pyridinyl)-N'-(1-methylethyl)urea was 2.9 grams; m.p. 77°–79° C. The nmr spectrum was consistent with the proposed structure.

Plant Regulator Utility

Plant growth regulators are used to modify plants by changing the rate or pattern, or both, of their response to internal and external factors that govern all stages of development from germination through vegetative growth, reproductive development, maturity and senescence. In addition, harvest aids, ripening agents, and chemicals for post-harvest preservation may be considered plant regulators. Plant regulators may be applied directly to a plant or to the soil in the vicinity of the plant to alter its life processes or morphological structure in some beneficial way, for example to enhance yield, improve quality, facilitate harvesting or otherwise advantageously modify growth and development. Such beneficial effects may include, but are not limited to, root initiation; set, development, ripening and abscission of fruits; plant size and shape; suppression of lodging; control of axillary buds and lateral shoots; metabolism regulation, including senescence; breaking or enforcing dormancy in seeds, buds, and storage organs; promotion or delay of flowering; defoliation; desiccation; and growth promotion under stress. Sometimes the same compound can both inhibit and promote growth, depending upon the rate of application.

The pyridinylurea compounds of the invention exhibit various forms of plant regulator activity when tested in vitro and in whole plant assays as described more particularly hereinbelow. Briefly, such activity is apparent in preemergence and post-emergence plant response screens on a variety of plants, particularly soybean and cotton, where morphological responses include stunting, axillary growth stimulation, nastic response, defoliation, darker green basal leaves, and some herbicidal activity. In antisenescence assays, compounds of the invention cause retention of chlorophyll in excised wheat leaves and in soybean leaves and pods, while reducing abscission, thus indicating ability to retard senescence.

The plant regulators of this invention are effectively employed as plant regulators in a number of broadleafed and grain crops, for example, soybean, lima bean, wheat, rice, corn, sorghum, and cotton, and turf grasses.

The plant regulator compounds, like most agricultural chemicals, are generally not applied full strength, but are formulated with agriculturally acceptable carriers or extenders (diluents) normally employed for facilitating the dispersion of active ingredients and various additives, and optionally with other active ingredients, recognizing that the formulation and mode of application of the active component may affect the activity of the material. The present compounds may be applied, for example, as powders or liquids, the choice of application varying with the plant species and environmental factors present at the particular locus of application. Thus, the compounds may be formulated as emulsifiable concentrates, wettable powders, flowable formulations, solutions, dispersions, suspensions and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% weight. Provided below is a general description of representative formulations which may be employed for dispersion of the plant regulators of the present invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

The following are specific examples of emulsifiable concentrate formulations suitable for use in the present invention:

| | % by Wt. |
|---|---|
| Formulation 1: | |
| Active ingredient | 53.01 |
| Blend of alkylbenzenesulfonate salt and polyoxyethylene ethers | 6.00 |
| Epoxidized soybean oil | 1.00 |
| Xylene | 39.99 |
| Total | 100.00 |
| Formulation 2: | |
| Active ingredient | 10.00 |
| Blend of alkylbenzenesulfonate salt and polyoxyethylene ethers | 4.00 |
| Xylene | 86.00 |

|  | % by Wt. |
|---|---|
| Total | 100.00 |

Wettable powders are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp < 100° C.) are suitably formulated in the concentration range of 5 to 50% by weight, usually from 10 to 30%; high melting solids (mp > 100° C.) being formulated in the range of 5 to 95% by weight, usually 50 to 85%. An agriculturally acceptable carrier or diluent, frequently including a small amount of a surfactant to facilitate wetting, dispersion and suspension, accounts for the balance of the formulation.

The following are specific examples of wettable powder formulations suitable for use in the present invention:

|  | % by Wt. |
|---|---|
| Formulation 3: |  |
| Active ingredient | 25.00 |
| Base: | 75.00 |
| 2% Sodium ligninsulfonate |  |
| 2% Sodium alkylnaphthalenesulfonate |  |
| 96% Attapulgite clay |  |
| Total | 100.00 |
| Formulation 4: |  |
| Active ingredient | 90.00 |
| Dioctyl sodium sulfosuccinate | 0.10 |
| Synthetic fine silica | 9.90 |
| Total | 100.00 |
| Formulation 5: |  |
| Active ingredient | 20.00 |
| Sodium alkylnaphthalenesulfonate | 1.00 |
| Sodium ligninsulfonate | 4.00 |
| Attapulgite clay | 75.00 |
| Total | 100.00 |
| Formulation 6: |  |
| Active ingredient | 25.00 |
| Base: | 75.00 |
| 96% hydrated aluminum magnesium silicate |  |
| 2% powdered sodium ligninsulfonate |  |
| 2% powdered anionic sodium alkyl-naphthalenesulfonate |  |
| Total | 100.00 |

Flowable formulations are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations suitable for use in the present invention:

|  | % by Wt. |
|---|---|
| Formulation 7: |  |
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylinic alcohols | 2.50 |
| Xanthan gum | 0.08 |
| Total | 100.00 |
| Formulation 8: |  |
| Active ingredient | 45.00 |
| Water | 48.50 |
| Purified smectite clay | 2.00 |
| Xanthan gum | 0.50 |
| Sodium alkylnathpthalenesulfonate | 1.00 |
| Acetylinic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively nonvolatile solvent such as water, corn oil, kerosene, propylene glycol, or other suitable solvents. This type of formulation is particularly useful for ultra low volume application.

The following illustrate specific suspensions which are suitable for use in the present invention:

| Formulation 9-Oil Suspension: | % by Wt. |
|---|---|
| Active ingredient | 5.42 |
| Emulsifier A | 5.00 |
| Emulsifier B | 5.00 |
| Suspending agent | 5.00 |
| Carrier-diluent | 79.58 |
| Total | 100.00 |

In formulation 9 Emulsifier A is the anionic free acid of a complex organic ester sold under the trademark and designation "GAFAC RE-410." Emulsifier B is a formulated nonionic concentrate sold under the trademark and designation "FloMo 200-4." The suspending agent is a bentonite clay sold under the trademark and designation "Bentone 34." The carrier-diluent is a mineral oil of viscosity 60 SUS sold under the trademark and designation "Sunspray 6N Oil."

| Formulation 10-Aqueous Suspension | % by Wt. |
|---|---|
| Active ingredient | 4.92 |
| Antimicrobial agent | 0.05 |
| Foam suppressant | 0.10 |
| Surfactant C | 2.60 |
| Surfactant D | 0.40 |
| Thickener | 0.35 |
| Suspending agent | 0.45 |

| Formulation 10-Aqueous Suspension | % by Wt. |
|---|---|
| Propylene glycol | 6.00 |
| Water | 85.13 |
| Total | 100.00 |

The antimicrobial agent is sodium o-phenylphenate tetrahydrate sold under the trademark and designation "Dowacide A". The foam suppressant is a water dilutable silicone emulsion sold under the trademark and designation "Dow Corning AF". Surfactant C is a nonionic paste of a condensate of ethylene oxide with a hydrophobic base formed by condensing propylene oxide with propylene glycol, sold under the trademark and designation "Pluronic P-84." Surfactant D is an anionic liquid comprising the sodium salt of a complex organic phosphate ester, sold under the trademark and designation "GAFAC LO-529." The thickener is a xantham gum sold under the trademark and designation "Kelzan-M". The suspending agent is a colloidal magnesium aluminum silicate sold under the trademark and designation "Veegum."

The concentration of the compound in use dilution is normally in the range of about 2% to about 0.1%. Many variations of spraying and dusting compositions in the art may be used by substituting or adding a compound of this invention into compositions known or apparent to the art.

The compositions may be formulated and applied with other suitable active ingredients, including nematicides, insecticides, acaricides, fungicides, other plant regulators, herbicides, fertilizers and other agricultural chemicals.

In applying the foregoing chemicals, an effective growth regulating amount of the active ingredient must be employed. While the application rate will vary widely depending on the choice of compound, the formulation and mode of application, the plant species being treated, the planting density and the growth response desired, a suitable use rate may be in the range of 0.01 to 10 kg/hectare, preferably 0.05 to about 5 kg/hectare. The compounds may be applied directly to a plant or to the soil or other locus of the plant.

The compounds of the invention were tested for plant regulator activity, first in a whole plant response screen and then in excised wheat leaf and soybean whole plant antisenescence tests.

Plant Response Screen

In this assay the test compounds are applied as water-acetone (1:1) solutions, containing 0.5% v/v sorbitan monolaurate solubilizer, at a rate equivalent to 8.0 kg/ha, preemergently to planted seeds of test plants and postemergently to foliage of test plants. The test plants were soybean, cotton, corn, wheat, field bindweed, morningglory, velvetleaf, barnyardgrass, green foxtail and johnsongrass.

All of the test compounds exhibited various forms and degrees of plant regulator activity although not against all of the plants and to the same extent in each case. Generally, the test compounds were more active when applied postemergently. The soybean and cotton plants were particularly responsive as evidenced by one or more of stunting, axillary growth stimulation, nastic response, defoliation, and darker green basal leaves. Morphological responses observed were stem strengthening in grasses, intumescence, leaf alteration and growth stimulation in the form of larger leaf area and/or internode distance. Some herbicidal activity was exhibited at the exceptionally high application rate of the test.

Wheat Leaf Antisenescence

1. Initial Test

In this test leaves were excised from wheat seedlings (*Triticum aestivum* cv. Prodaz), weighed and placed in vials containing solutions of test compound in water-acetone (1:1) at concentrations of 25 ppm and 2.5 ppm. Wheat leaves were similarly placed in vials containing only deionized water, as controls. After four days of incubation at 30° C. in the dark, the test vials were examined visually and given a numeric rating of 0 (color similar to color of the leaves in the control vials) or 1 (more green than the leaves in the control vials). The control leaves had yellowed, indicating loss of chlorophyll. The test results, set forth in Table II (appended), show that compounds 2-16, 22, 25, 31, 33, 38 and 44 caused retention of chlorphyll at both 25 ppm and 2.5 ppm as compared with the control, and that compounds, 1, 17-21, 23, 24, 26, 32, 34, 35, 46 and 47 were active at 25 ppm. The apparent inactivity of the remaining compounds in Table II may be caused by limited solubility in the water-acetone test solvent.

2. Chlorophyll Retention—Senescence Inhibition ($SI_{50}$)

Compounds of the invention were tested for their ability to retain the chlorophyll in freshly excised wheat leaves as compared with frozen wheat leaf controls which, theoretically, retain 100% of their chlorophyll. In the test, excised wheat leaves were weighed and placed in vials of water-acetone (1:1) solutions of test compounds at concentrations ranging from $10^{-5}$ to $10^{-9}$ molar. Vials containing the leaves in water alone were used as controls. After 4 days incubation at 30° C. in the dark, the chlorophyll content of the excised leaves was determined by extracting the leaves with methanol or other solvent. The absorbances of the chlorophyll-containing extracts were determined spectrophotometrically at 652 nm and converted to micrograms of chlorophyll/gram of fresh leaf weight for test vials and controls by the formula $$A \frac{652 \text{ nm}}{\text{fresh weight in grams}} \times 299 = \mu g \text{ chlorophyll/g fresh weight}$$

The calculated results were then divided by the micrograms of chlorophyll/gram fresh weight of the frozen leaf control and the result multiplied by 100 to give percent of chlorophyll retained as compared with the frozen wheat leaf control. The percent chlorophyll retained in the wheat leaves by the various concentrations of test chemical was plotted against the negative log of the concentration. From the resulting graph, the negative log of the concentration that would retain 50% of the chlorophyll ($SI_{50}$) was determined. The greater the $SI_{50}$ value, the more active the test chemical as a senescence inhibitor.

The results are given in Table III (appended) for averages of three replicates from which it will be seen that all of the test compounds caused some retention of chlorophyll, the average $SI_{50}$ value being 5.7. Compounds 3, 5 and 7 have $SI_{50}$ values averaging 6.0 or higher, making these compounds the most active of the test.

Soybean Utility Test

Compounds of the invention were sprayed onto the foliage of soybean test plants at rates of 2.0, 0.50, and 0.125 kg/ha. The test compounds were sprayed as water-acetone (1:1) solutions containing 2% sorbitan monolaurate emulsifier. The soybean test plants were at the beginning seed stage at the time of spraying.

Approximately 15 days post-treatment, the leaves and pods of the soybean test plants were inspected for senescence. Leaf and pod senescence was measured using a rating scale of 0-5, 0 indicating leaf and pod abscission and 5 being 100% green leaves and pods. The soybean test plants were inspected periodically up to 43 days. At each inspection the leaf and pod senescence was measured using the aforementioned rating. Graphs were prepared for each test chemical in which the mean leaf senescence ratings were plotted against the corresponding days post-treatment. A second set of graphs was prepared in which the mean pod senescence ratings were plotted against the corresponding days post-treatment. Leaf and pod senescence ratings vs the corresponding days post-treatment for the untreated control were plotted on these same graphs. Using the graphs, the number of days delay in reaching 50% leaf senescence (leaf senescence rating=2.5) for each test chemical, as compared to the untreated control, was determined. The process was repeated with the mean pod senescence ratings to determine the number of days delay in reaching 50% pod senescence (2.5) for each test chemical.

Table IV (appended) gives the results from which it will be seen that compound 7 delayed both leaf and pod senescence.

TABLE I

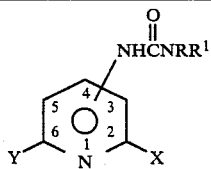

| Cmpd. No. | R | $R^1$ | X | Y | Name | Empirical Formula/ m.p./b.p. |
|---|---|---|---|---|---|---|
| 1 | $CH_3$ | H | Cl | H | N—(2-chloro-4-pyridinyl)-N'—methylurea | $C_7H_8ClN_3O$ S(—) |
| 2 | $C_2H_5$ | H | Cl | H | N—(2-chloro-4-pyridinyl)-N'—ethylurea | $C_8H_{10}ClN_3O$ L(—) |
| 3 | $CH_2CH_2Cl$ | H | Cl | H | N—(2-chloro-4-pyridinyl)-N'—(2-chloroethyl)urea | $C_8H_9Cl_2N_3O$ S(87–89° C.) |
| 4 | $CH_2CF_3$ | H | Cl | H | N—(2-chloro-4-pyridinyl)-N'—(2,2,2-trifluoroethyl)urea | $C_8H_9ClF_3N_3O$ S(168–170° C.) |
| 5 | $C_3H_7$ | H | Cl | H | N—(2-chloro-4-pyridinyl)-N'—propylurea | $C_9H_{12}ClN_3O$ L(—) |
| 6* | $CH(CH_3)_2$ | H | Cl | H | N—(2-chloro-3-pyridinyl)-N'—(1-methylethyl)urea | $C_9H_{12}ClN_3O$ S(150–152° C.) |
| 7 | $CH(CH_3)_2$ | H | Cl | H | N—(2-chloro-4-pyridinyl)-N'—(1-methylethyl)urea | $C_9H_{12}ClN_3O$ S(142–146.5° C.) |
| 8 | $CH_2CH_2CH_2Cl$ | H | Cl | H | N—(2-chloro-4-pyridinyl)-N'—(3-chloropropyl)urea | $C_9H_{11}Cl_2N_3O$ L(—) |
| 9 | $CH_2CF_2CF_3$ | H | Cl | H | N—(2-chloro-4-pyridinyl)-N'—(2,2,3,3,3-pentafluoropropyl)urea | $C_9H_7ClF_5N_3O$ S(60–68° C.) |
| 10 | $CH_2CH=CH_2$ | H | Cl | H | N—(2-chloro-4-pyridinyl)-N'—(2-propenyl)urea | $C_9H_{10}ClN_3O$ L(—) |
| 11 | $C_4H_9$ | H | Cl | H | N—(2-chloro-4-pyridinyl)-N'—butylurea | $C_{10}H_{14}ClN_3O$ L(—) |
| 12(1) | $CH(CH_3)C_2H_5$ | H | Cl | H | (±)-N—(2-chloro-4-pyridinyl)-N'—(1-methylpropyl)urea | $C_{10}H_{14}ClN_3O$ S(137–139° C.) |
| 13(2) | $CH(CH_3)C_2H_5$ | H | Cl | H | (+)-N—(2-chloro-4-pyridinyl)-N'—(1-methylpropyl)urea | $C_{10}H_{14}ClN_3O$ S(138–140° C.) |
| 14(2) | $CH(CH_3)C_2H_5$ | H | Cl | H | (−)-N—(2-chloro-4-pyridinyl)-N'—(1-methylpropyl)urea | $C_{10}H_{14}ClN_3O$ S(138–140° C.) |
| 15 | $CH_2CH(CH_3)_2$ | H | Cl | H | N—(2-chloro-4-pyridinyl)-N'—(2-methylpropyl)urea | $C_{10}H_{14}ClN_3O$ S(96–99° C.) |
| 16 | $C(CH_3)_3$ | H | Cl | H | N—(2-chloro-4-pyridinyl)-N'—(1,1-dimethylethyl)urea | $C_{10}H_{14}ClN_3O$ S(153–155° C.) |
| 17(1) | $CH(CH_2OH)C_2H_5$ | H | Cl | H | (±)-N—(2-chloro-4-pyridinyl)-N'—(1-hydroxymethylpropyl)urea | $C_{10}H_{14}ClN_3O_2$ S(63–71° C.) |
| 18(3) | $CH(CH_2OH)C_2H_5$ | H | Cl | H | (+)-N—(2-chloro-4-pyridinyl)-N'—(1-hydroxymethylpropyl)urea | $C_{10}H_{14}ClN_3O_2$ S(100–104° C.) |
| 19(4) | $CH(CH_2OH)C_2H_5$ | H | Cl | H | (−)-N—(2-chloro-4-pyridinyl)-N'—(1-hydroxymethylpropyl)urea | $C_{10}H_{14}ClN_3O_2$ S(118–126° C.) |
| 20 | $C_5H_{11}$ | H | Cl | H | N—(2-chloro-4-pyridinyl)-N'—pentylurea | $C_{11}H_{16}ClN_3O$ L(—) |
| 21(1) | $CH(CH_3)C_3H_7$ | H | Cl | H | (±)-N—(2-chloro-4-pyridinyl)-N'—(1-methylbutyl)urea | $C_{11}H_{16}ClN_3O$ S(65–70° C.) |
| 22 | $CH(C_2H_5)_2$ | H | Cl | H | N—(2-chloro-4-pyridinyl)-N'—(1-ethylpropyl)urea | $C_{11}H_{16}ClN_3O$ S(134–136° C.) |
| 23(1) | $CH_2CH(CH_3)C_2H_5$ | H | Cl | H | (±)-N—(2-chloro-4-pyridinyl)-N'—(2-methylbutyl)urea | $C_{11}H_{16}ClN_3O$ L(—) |
| 24 | $CH_2CH_2CH(CH_3)_2$ | H | Cl | H | N—(2-chloro-4-pyridinyl)-N'—(3-methylbutyl)urea | $C_{11}H_{16}ClN_3O$ S(48–54° C.) |
| 25 | $C(CH_3)_2C_2H_5$ | H | Cl | H | N—(2-chloro-4-pyridinyl)- | $C_{11}H_{16}ClN_3O$ |

TABLE I-continued $$\text{structure: pyridine ring with NHC(=O)NRR}^1 \text{ at position 4, X at position 2, Y at position 6}$$

| Cmpd. No. | R | R¹ | X | Y | Name | Empirical Formula/ m.p./b.p. |
|---|---|---|---|---|---|---|
| | | | | | N'—(1,1-dimethylpropyl)urea | S(123–125° C.) |
| 26 | $CH_2C(CH_3)_3$ | H | Cl | H | N—(2-chloro-4-pyridinyl)- N'—(2,2-dimethylpropyl)urea | $C_{11}H_{16}ClN_3O$ S(55–64° C.) |
| 27 | $C_6H_{13}$ | H | Cl | H | N—(2-chloro-4-pyridinyl)- N'—hexylurea | $C_{12}H_{18}ClN_3O$ L(—) |
| 28 | $C_7H_{15}$ | H | Cl | H | N—(2-chloro-4-pyridinyl)- N'—heptylurea | $C_{13}H_{20}ClN_3O$ L(—) |
| 29 | $C_8H_{17}$ | H | Cl | H | N—(2-chloro-4-pyridinyl)- N'—octylurea | $C_{14}H_{22}ClN_3O$ L(—) |
| 30 | $C(CH_3)_2CH_2C(CH_3)_2CH_3$ | H | Cl | H | N—(2-chloro-4-pyridinyl)- N'—(1,1,3,3-tetramethylbutyl)urea | $C_{14}H_{22}ClN_3O$ S(—) |
| 31 | cyclopropyl | H | Cl | H | N—(2-chloro-4-pyridinyl)- N'—cyclopropyl | $C_9H_{10}ClN_3O$ S(117–121° C.) |
| 32 | cyclobutyl | H | Cl | H | N—(2-chloro-4-pyridinyl)- N'—cyclobutylurea | $C_{10}H_{12}ClN_3O$ S(70–105° C.) |
| 33 | cyclopentyl | H | Cl | H | N—(2-chloro-4-pyridinyl)- N'—cyclopentylurea | $C_{11}H_{14}N_3O$ S(119–121° C.) |
| 34 | cyclohexyl | H | Cl | H | N—(2-chloro-4-pyridinyl)- N'—cyclohexylurea | $C_{12}H_{16}ClN_3O$ S(143–152° C.) |
| 35 | cycloheptyl | H | Cl | H | N—(2-chloro-4-pyridinyl)- N'—cycloheptylurea | $C_{13}H_{18}ClN_3O$ S(60–70° C.) |
| 36 | cyclooctyl | H | Cl | H | N—(2-chloro-4-pyridinyl)- N'—cyclooctylurea | $C_{14}H_{20}ClN_3O$ S(65–80° C.) |
| 37[1] | 1-phenylethyl | H | Cl | H | (±)-N—(2-chloro-4-pyridinyl)- N'—(1-phenylethyl)urea | $C_{14}H_{14}ClN_3O$ S(58–68° C.) |
| 38[3] | 1-phenylethyl | H | Cl | H | (+)-N—(2-chloro-4-pyridinyl)- N'—(1-phenylethyl)urea | $C_{14}H_{14}ClN_3O$ S(—) |
| 39[4] | 1-phenylethyl | H | Cl | H | (−)-N—(2-chloro-4-pyridinyl)- N'—(1-phenylethyl)urea | $C_{14}H_{14}ClN_3O$ S(—) |
| 40* | $CH_3$ | H | H | $OCH_3$ | N—(6-methoxy-3-pyridinyl)- N'—methylurea | $C_8H_{11}N_3O_2$ |
| 41* | $CH_3$ | H | H | $OC_4H_9$ | N—(6-butoxy-3-pyridinyl)- N'—methylurea | $C_{11}H_{17}N_3O_2$ |
| 42 | $CH_2CH_2OH$ | H | Cl | Cl | N—(2,6-dichloro-4-pyridinyl)- N'—(2-hydroxyethyl)urea | $C_8H_9Cl_2N_3O_2$ |
| 43* | $CH(CH_3)_2$ | H | H | Cl | N—(6-chloro-3-pyridinyl) N'—(1-methylethyl)urea | $C_9H_{12}ClN_3O$ S(162–164° C.) |
| 44 | $CH(CH_3)_2$ | H | Br | H | N—(2-bromo-4-pyridinyl)- N'—(1-methylethyl)urea | $C_9H_{12}BrN_3O$ S(136–138° C.) |
| 45* | $CH(CH_3)_2$ | H | H | $OCH_3$ | N—(6-methoxy-3-pyridinyl)- N'—(1-methylethyl)urea | $C_{10}H_{15}N_3O_2$ S(167–168° C.) |
| 46 | $CH(CH_3)_2$ | H | $OCH_3$ | H | N—(2-methoxy-4-pyridinyl)- N'—(1-methylethyl)urea | $C_{10}H_{15}N_3O_2$ S(114–117° C.) |
| 47 | $CH(CH_3)_2$ | H | $OC_3H_7$ | H | N—(2-propoxy-4-pyridinyl)- N'—(1-methylethyl)urea | $C_{12}H_{19}N_3O_2$ S(77–79° C.) |
| 48* | $CH(CH_3)_2$ | H | H | $OC_4H_9$ | N—(6-butoxy-3-pyridinyl)- N'—(1-methylethyl)urea | $C_{13}H_{21}N_3O_2$ S(130–132° C.) |
| 49 | $C_3H_7$ | H | Cl | Cl | N—(2,6-dichloro-4-pyridinyl)- N'—propylurea | $C_9H_{14}N_3O$ |
| 50 | $CH_3$ | $C(CH_3)_3$ | Cl | H | N—(2-chloro-4-pyridinyl)-N'—methyl- N'—(1,1-dimethylethyl)urea | $C_{11}H_{16}ClH_3O$ S(99–102° C.) |
| 51 | cyclopentyl | $CH_3$ | Cl | H | N—(2-chloro-4-pyridinyl)- N—methyl-N'—cyclopentylurea | $C_{12}H_{16}ClN_3O$ S(106–108° C.) |
| 52 | $(CH_2)_2OCH_3$ | H | Cl | H | N—(2-chloro-4-pyridinyl)- N'—(2-methoxyethyl)urea | $C_9H_{12}ClN_3O_2$ |
| 53 | $(CH_2)_3OCH_3$ | H | Cl | H | N—(2-chloro-4-pyridinyl)- N'—(3-methoxypropyl)urea | $C_{10}H_{14}ClN_3O_2$ |
| 54 | $(CH_2)_2N(CH_3)_2$ | H | Cl | H | N—(2-chloro-4-pyridinyl)- N'—(2-dimethylamineoethyl)urea | $C_{10}H_{15}ClN_4O$ |
| 55 | $(CH_2)_3N(CH_3)_2$ | H | Cl | H | N—(2-chloro-4-pyridinyl)- N'—(3-dimethylaminopropyl)urea | $C_{11}H_{17}ClN_4O$ |
| 56 | $CH(CH_3)_2$ | H | $CF_3$ | H | N—(2-trifluoromethyl-4-pyridinyl)- N'—(1-methylethyl)urea | $C_{10}H_{12}F_3N_3O$ |
| 57 | $CH(CH_3)_2$ | H | $C_3F_7$ | H | N—(2-heptafluoropropyl-4-pyridinyl)- N'(1-methylethyl)urea | $C_{12}H_{12}F_7H_3O$ |
| 58 | —$(CH_2)_4$— | | Cl | H | N—(2-chloro-4-pyridinyl)-1- pyrrolidinecarboxamide | $C_{10}H_{12}ClN_3O$ |
| 59 | —$(CH_2)_5$— | | Cl | H | N—(2-chloro-4-pyridinyl)-1- piperidinecarboxamide | $C_{11}H_{14}ClN_3O$ |
| 60 | —$(CH_2)_6$— | | Cl | H | N—(2-chloro-4-pyridinyl)- | $C_{12}H_{16}ClH_3O$ |

TABLE I-continued

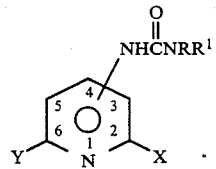

| Cmpd. No. | R | R¹ | X | Y | Name | Empirical Formula/ m.p./b.p. |
|---|---|---|---|---|---|---|
| | | | | | 1H—azepine-1-carboxamide | |

*The urea group (NHCONRR¹) is in the 3-position of the pyridine ring. In all other compounds of Table I the substituted urea is in the 4-position.
[1] a racemic mixture
[2] a stereo isomer - configuration uncertain
[3] R—[+] stereoisomer
[4] S—[−] stereoisomer

TABLE II

Antisenescence Initial Assay - Wheatleaf Chlorophyll Retention

| Compound Number | Concentration (ppm) | Visual Evaluation of Wheat Leaves in the Test Solutions |
|---|---|---|
| 1 | 25.0 | 1 |
| | 2.5 | 0 |
| 2 | 25.0 | 1 |
| | 2.5 | 1 |
| 3 | 25.0 | 1 |
| | 2.5 | 1 |
| 4 | 25.0 | 1 |
| | 2.5 | 1 |
| 5 | 25.0 | 1 |
| | 2.5 | 1 |
| 6 | 25.0 | 1 |
| | 2.5 | 1 |
| 7 | 25.0 | 1 |
| | 2.5 | 1 |
| 8 | 25.0 | 1 |
| | 2.5 | 1 |
| 9 | 25.0 | 1 |
| | 2.5 | 1 |
| 10 | 25.0 | 1 |
| | 2.5 | 1 |
| 11 | 25.0 | 1 |
| | 2.5 | 1 |
| 12 | 25.0 | 1 |
| | 2.5 | 1 |
| 13 | 25.0 | 1 |
| | 2.5 | 1 |
| 14 | 25.0 | 1 |
| | 2.5 | 1 |
| 15 | 25.0 | 1 |
| | 2.5 | 1 |
| 16 | 25.0 | 1 |
| | 2.5 | 1 |
| 17 | 25.0 | 1 |
| | 2.5 | 0 |
| 18 | 25.0 | 1 |
| | 2.5 | 0 |
| 19 | 25.0 | 1 |
| | 2.5 | 0 |
| 20 | 25.0 | 1 |
| | 2.5 | 0 |
| 21 | 25.0 | 1 |
| | 2.5 | 0 |
| 22 | 25.0 | 1 |
| | 2.5 | 1 |
| 23 | 25.0 | 1 |
| | 2.5 | 0 |
| 24 | 25.0 | 1 |
| | 2.5 | 0 |
| 25 | 25.0 | 1 |
| | 2.5 | 1 |
| 26 | 25.0 | 1 |
| | 2.5 | 0 |
| 27 | 25.0 | 0 |
| | 2.5 | 0 |
| 28 | 25.0 | 0 |
| | 2.5 | 0 |
| 29 | 25.0 | 0 |
| | 2.5 | 0 |
| 30 | 25.0 | 0 |
| | 2.5 | 0 |
| 31 | 25.0 | 1 |
| | 2.5 | 1 |
| 32 | 25.0 | 1 |
| | 2.5 | 0 |
| 33 | 25.0 | 1 |
| | 2.5 | 1 |
| 34 | 25.0 | 1 |
| | 2.5 | 0 |
| 35 | 25.0 | 1. |
| | 2.5 | 0 |
| 36 | 25.0 | 0* |
| | 2.5 | 0 |
| 37 | 25.0 | 0* |
| | 2.5 | 0 |
| 38 | 25.0 | 1(0) |
| | 2.5 | 1(0) |
| 39 | 25.0 | 0* |
| | 2.5 | 0 |
| 42 | 25.0 | 0 |
| | 2.5 | 0 |
| 44 | 25.0 | 1 |
| | 2.5 | 1 |
| 46 | 25.0 | 1 |
| | 2.5 | 0 |
| 47 | 25.0 | 1 |
| | 2.5 | 0 |
| 51 | 25.0 | 1 |
| | 2.5 | 0 |

TABLE III

Wheatleaf Chlorophyll Retention - SI₅₀ Values

| Cmpd No. | Molar Conc. | Percent Chlorophyll Retained as Compared to Frozen Wheat Leaf Check | $SI_{50}$ |
|---|---|---|---|
| 1 | $10^{-4}$ | 45 | — |
| | $10^{-5}$ | 40 | |
| | $10^{-6}$ | 45 | |
| 2 | $10^{-5}$ | 62 | 5.5 |
| | $10^{-6}$ | 23 | |
| | $10^{-7}$ | 13 | |
| | $10^{-8}$ | 18 | |
| 3 | $10^{-5}$ | 73 | 6.3 |
| | $10^{-6}$ | 66 | |
| | $10^{-7}$ | 29 | |
| 4 | $10^{-5}$ | 51 | 5.2 |
| | $10^{-6}$ | 37 | |
| | $10^{-7}$ | 19 | |

TABLE III-continued

Wheatleaf Chlorophyll Retention - $SI_{50}$ Values

| Cmpd No. | Molar Conc. | Percent Chlorophyll Retained as Compared to Frozen Wheat Leaf Check | $SI_{50}$ |
|---|---|---|---|
| 5 | $10^{-8}$ | 9 | |
| | $10^{-5}$ | 64,78 | 6.3, 6.5 |
| | $10^{-6}$ | 59 | |
| | $10^{-7}$ | 30 | |
| | $10^{-8}$ | 20 | |
| 7 | $10^{-5}$ | 73,60,67 | 6.1, 5.8, 5.7 |
| | $10^{-6}$ | 57,30,38 | |
| | $10^{-7}$ | 14,22,15 | |
| | $10^{-8}$ | 29,13 | |
| 8 | $10^{-4}$ | 43 | — |
| | $10^{-5}$ | 41 | |
| | $10^{-6}$ | 22 | |
| | $10^{-7}$ | 27 | |
| 10 | $10^{-5}$ | 68,73 | 5.6, 6.0 |
| | $10^{-6}$ | 39 | |
| | $10^{-7}$ | 21 | |
| | $10^{-8}$ | 13 | |
| 11 | $10^{-5}$ | 58 | 5.9 |
| | $10^{-6}$ | 52 | |
| | $10^{-7}$ | 34 | |
| | $10^{-8}$ | 42 | |
| 12 | $10^{-5}$ | 54.4 | 5.7 |
| | $10^{-6}$ | 33.0 | |
| | $10^{-7}$ | 6.0 | |
| 15 | $10^{-8}$ | 4.9 | |
| | $10^{-5}$ | 61 | 5.8 |
| | $10^{-6}$ | 46 | |
| | $10^{-7}$ | 23 | |
| | $10^{-8}$ | 16 | |
| 16 | $10^{-5}$ | 58 | 5.7 |
| | $10^{-6}$ | 35 | |
| | $10^{-7}$ | 26 | |
| | $10^{-8}$ | 12 | |
| 20 | $10^{-5}$ | 27 | — |
| | $10^{-6}$ | 12 | |
| | $10^{-7}$ | 7 | |
| | $10^{-8}$ | 5 | |
| 31 | $10^{-5}$ | 66,57 | 5.5, 5.7 |
| | $10^{-6}$ | 40,24 | |
| | $10^{-7}$ | 18,7 | |
| | $10^{-8}$ | 17,7 | |
| 32 | $10^{-4}$ | 44 | 5.8 |
| | $10^{-5}$ | 57 | |
| | $10^{-6}$ | 35 | |
| 33 | $10^{-5}$ | 60 | 5.6 |
| | $10^{-6}$ | 23 | |
| | $10^{-7}$ | 13 | |
| | $10^{-8}$ | 7 | |
| 34 | $10^{-4}$ | 58,60 | 4.6, 4.7 |
| | $10^{-5}$ | 34,49 | |
| | $10^{-6}$ | 18,35 | |
| 38 | $10^{-5}$ | 29 | — |
| | $10^{-6}$ | 27 | |
| | $10^{-7}$ | 22 | |
| | $10^{-8}$ | 26 | |
| 39 | $10^{-5}$ | 37 | — |
| | $10^{-6}$ | 26 | |
| | $10^{-7}$ | 24 | |
| 42 | $10^{-5}$ | 32 | — |
| | $10^{-6}$ | 29 | |
| | $10^{-7}$ | 25 | |
| | $10^{-8}$ | 21 | |
| 44 | $10^{-5}$ | 55 | 5.4 |
| | $10^{-6}$ | 39 | |
| | $10^{-7}$ | 22 | |
| | $10^{-8}$ | 16 | |
| 47 | $10^{-4}$ | 38 | — |
| | $10^{-5}$ | 26 | |
| | $10^{-6}$ | 20 | |
| Frozen Wheat Leaf Check | | 100 | |
| Water Control | | 22 | |

TABLE IV

Leaf and Pod Senescence of Soybean Test Plants Treated at the Beginning Seed Stage

| Cmpd No. | Rate of Application (kg/ha) | Leaf Senescence Ratings Days Post-Treatment | | | | | | | | | | Pod Senescence Rating Days Post-Treatment | | | | | | | | | | Days Senescence Delayed as Compared to the Untreated Check | |
|---|---|---|---|---|---|---|---|---|---|---|---|---|---|---|---|---|---|---|---|---|---|---|---|
| | | 20 | 21 | 22 | 28 | 29 | 31 | 34 | 35 | 36 | 42 | 43 | 20 | 21 | 22 | 28 | 29 | 31 | 34 | 35 | 36 | 42 | 43 | Leaf | Pod |
| 5 | 2.0 | | | 3.8 | 1.8 | | | | 1.0 | | 1.0 | | | | 3.8 | 2.2 | | | | 1.0 | | 1.0 | Not calculable | |
| | 0.5 | | | 2.8 | 1.4 | | | | 0.4 | | 0.2 | | | | 3.8 | 1.8 | | | | 1.0 | | 1.0 | | |
| | 0.125 | | | 3.8 | 1.8 | | | | 1.2 | | 1.0 | | | | 3.8 | 1.6 | | | | 1.0 | | 1.0 | | |
| Untreated check | | | | 3.8 | 1.8 | | | | 0.8 | | 0.2 | | | | 3.8 | 1.8 | | | | 1.0 | | 1.0 | | |
| 7 | 2.0 | | | 3.4 | 2.6 | | | | 1.0 | | 0.6 | | | | 3.6 | 2.6 | | | | 1.0 | | 1.0 | Not calculable | |
| | 0.5 | | | 3.2 | 1.6 | | | | 0.8 | | 0.4 | | | | 3.2 | 1.8 | | | | 1.0 | | 1.0 | | |
| | 0.125 | | | 1.6 | 1.2 | | | | 0.8 | | 0.6 | | | | 2.0 | 1.2 | | | | 1.0 | | 1.0 | | |
| Untreated check | | | | 3.8 | 1.8 | | | | 0.8 | | 0.2 | | | | 3.8 | 1.8 | | | | 1.0 | | 1.0 | | |
| 7 | 2.0 | | 2.8 | | 1.6 | | | 0.8 | | | | | | 3.0 | | 1.6 | | | | | 1.0 | | | 5 | 2 |
| | 0.5 | | 3.0 | | 1.8 | | | 1.0 | | | | | | 3.0 | | 1.8 | | | | | 1.0 | | | 4 | 2 |
| | 0.125 | | 2.6 | | 1.2 | | | 0.4 | | | | | | 3.0 | | 1.4 | | | | | 1.0 | | | | |
| Untreated check | | | 2.2 | | 1.4 | | | 0.8 | | | | | | 2.6 | | 1.0 | | | | | 1.0 | | | | |
| 10 | 2.0 | | | 2.2 | 1.0 | | | | 0.4 | | 0.4 | | | | 2.2 | 1.4 | | | | 1.0 | | 1.0 | Not calculable | |
| | 0.5 | | | 2.4 | 1.4 | | | | 1.0 | | 1.0 | | | | 2.2 | 1.4 | | | | 1.0 | | 1.0 | | |
| Untreated check | | | | 3.8 | 1.8 | | | | 0.8 | | 0.2 | | | | 3.8 | 1.8 | | | | 1.0 | | 1.0 | | |

I claim:

1. Pyridinylurea compounds of the formula:

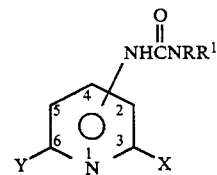

and acid addition salts thereof; wherein R is isopropyl, n-butyl, i-butyl, tert. butyl, sec. pentyl, tert. pentyl, cyclopropyl, or an alkyl($C_1$–$C_5$) group substituted with hydroxy, cycloalkyl($C_3$–$C_8$) or dialkylamino; $R^1$ is hydrogen or methyl; R and $R^1$ together with the nitrogen atom of the $NRR^1$ group optionally define a heterocycle selected from pyrrolidinyl, 3-pyrrolinyl, piperidinyl and azepinyl; X is hydrogen, halogen, haloalkyl, alkoxy, alkylthio or alkylsulfonyl; Y is hydrogen, halogen, haloalkyl, alkoxy, alkylthio or alkylsulfonyl; R, X and Y may each contain alkyl ($C_1$–$C_2$) atoms; and wherein the NHCONRR$^1$ group is bonded to the pyridinyl ring in the 4-position; provided that at least one of X and Y is other than hydrogen and provided further that when R$^1$ methyl then R is tert. butyl or cyclopentyl and when X and Y are halogen then R is cycloalkyl($C_5$–$C_7$) or isopropyl, and R, X and Y each contain 1–20 carbon atoms unless otherwise specified.

2. Compounds of claim 1 wherein R$^1$ is hydrogen.

3. Compounds of claim 1 wherein R$^1$ is hydrogen and Y is hydrogen.

4. Compounds of claim 1 wherein R$^1$ is hydrogen, and X and Y are halogen.

5. Compounds of claim 1 wherein R$^1$ is hydrogen, Y is hydrogen and X is halogen or haloalkyl.

6. A compound of claim 1 which is N-(2-chloro-4-pyridinyl)-N'-(1-methylethyl)urea.

7. A compound of claim 1 which is N-(2-chloro-4-pyridinyl)-N'-butylurea.

8. A compound of claim 1 which is N-(2-chloro-4-pyridinyl)-N'-(1,1-dimethylethyl)urea.

9. A compound of claim 1 which is N-(2-chloro-4-pyridinyl)-N'-(1,1-dimethylpropyl)urea.

10. A compound of claim 1 which is N-(2,6-dichloro-4-pyridinyl)-N'-(1-methylethyl).

11. A plant growth regulator composition comprising a plant regulating amount of a compound of claim 1 in admixture with an agriculturally acceptable carrier or extender.

12. A method of retarding senescence in plants which comprises applying to the plant a plant regulating amount of a compound of claim 1.

13. A method of retarding senescence in plants which comprises applying to the plant a plant regulating amount of a compound of claim 4.

14. A method of retarding senescence in plants which comprises applying to the plant a plant regulating amount of a compound of claim 5.

15. A method of retarding senescence in plants which comprises applying to the plant a plant regulating amount of a compound of claim 6.

16. A method of retarding senescence in plants which comprises applying to the plant a plant regulating amount of a compound of claim 7.

17. A method of retarding senescence in plants which comprises applying to the plant a plant regulating amount of the compound of claim 8.

18. A method of retarding senescence in plants which comprises applying to the plant a plant regulating amount of the compound of claim 9.

19. A method of retarding senescence in plants which comprises applying to the plant a plant regulating amount of the compound of claim 10.

20. A plant growth regulator composition comprising a plant regulating amount of a compound of claim 1 in admixture with an agriculturally acceptable carrier or extender.

21. A method of retarding senescence in soybean plants which comprises applying to the plant a plant regulating amount of a compound of claim 20.

22. Plant regulatory pyridinylurea compounds of claim 1 selected from:

N-(2-chloro-4-pyridinyl)-N'-(2,2,2-trifluoroethyl)urea
N-(2-chloro-4-pyridinyl)-N'-(1-methylethyl)urea
N-(2-chloro-4-pyridinyl)-N'-(2,2,3,3,3-pentafluoropropyl)urea
N-(2-chloro-4-pyridinyl)-N'-butylurea
N-(2-chloro-4-pyridinyl)-N'-(1-methylpropyl)urea
N-(2-chloro-4-pyridinyl)-N'-(1,1-dimethylethyl)urea
[N-(2-chloro-4-pyridinyl)-N'-(1-ethylpropyl)urea]
N-(2-chloro-4-pyridinyl)-N'-(1,1-dimethylpropyl)urea
N-(2-chloro-4-pyridinyl)-N'-cyclopropylurea
N-(2-bromo-4-pyridinyl)-N'-(1-methylethyl)urea
N-(2-chloro-4-pyridinyl)-N'-cyclopropyl-N'-methylurea
N-(2,6-dichloro-4-pyridinyl)-N'-cyclopentylurea
N-(2,6-dichloro-4-pyridinyl)-N'-cycloheptylurea
N-(2-chloro-4-pyridinyl)-N'-methyl-N'-(1,1-dimethylethyl)urea
N-(2,6-dichloro-4-pyridinyl)-N'-(1-methylethyl)urea
[N-(2-chloro-4-pyridinyl)-N'-methyl-N'-(1-methylpropyl)urea]
N-(2-chloro-4-pyridinyl)-N'-(1,1-dimethyl-3-hydroxypropyl)urea
N-(2-chloro-4-pyridinyl)-N'-(1,1-dimethyl-2-hydroxyethyl)urea
N-(2-chloro-4-pyridinyl)-N'-(2-methylpropyl)urea.

* * * * *

UNITED STATES PATENT AND TRADEMARK OFFICE
CERTIFICATE OF CORRECTION

PATENT NO. : 4,818,271
DATED : April 4, 1989
INVENTOR(S) : Robert N. Henrie, II

It is certified that error appears in the above—identified patent and that said Letters Patent is hereby corrected as shown below:

In the Abstract and columns 1 and 20, replace the formula with

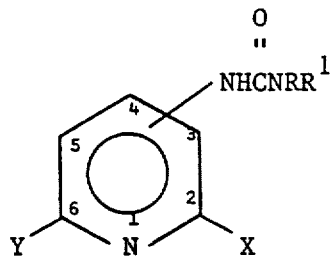

In column 20, line 68, delete "R, X and Y".

In column 21, line 1, may each contain alkyl $(C_1-C_2)$ atoms"

Signed and Sealed this

Thirteenth Day of March, 1990

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,818,271

DATED : April 4, 1989

INVENTOR(S) : ROBERT N. HENRIE, II

It is certified that error appears in the above-identified patent and that said Letters Patent is hereby corrected as shown below:

Column 20, claim 1, line 68: reads "alkyl, alkoxy, alkylthio or alkylsulfonyl; R, X and Y"

should read -- alkyl, alkoxy, alkylthio or alkylsulfonyl; --

Column 21, claim 1, line 1: reads "may each contain alkyl ($C_1$-$C_2$) atoms; and wherein the"

should read -- and wherein the --

Column 22, claim 22, line 1: reads "Plant regulatory pyridinylurea compounds of"

should read -- Plant regulatory pyridinylurea compounds --

Column 22, claim 22, line 2: reads "claim 1 selected from:"

should read -- selected from: --

UNITED STATES PATENT AND TRADEMARK OFFICE
CERTIFICATE OF CORRECTION

PATENT NO. : 4,818,271

DATED : April 4, 1989

INVENTOR(S) : ROBERT N. HENRIE, II

It is certified that error appears in the above-identified patent and that said Letters Patent is hereby corrected as shown below:

Column 22, claim 22, line 27:

cancel the following
"[N-(2-chloro-4-pyridinyl)-N'-(1-ethylpropyl)urea]"

Column 22, claim 22, lines 32 and 33:

reads
"N-(2-chloro-4-pyridinyl)-N'-cyclopropyl-N'-methylurea"

should read
-- N-(2-chloro-4-pyridinyl)-N'-cyclopropylmethyl-urea --

Column 22, claim 22, lines 39 and 40:

cancel the following
"[N-(2-chloro-4-pyridinyl)-N'-methyl-N'-(1-methylpropyl)urea]"

Signed and Sealed this

Fourteenth Day of August, 1990

*Attest:*

HARRY F. MANBECK, JR.

*Attesting Officer*     *Commissioner of Patents and Trademarks*